United States Patent [19]

Goldstein et al.

[11] Patent Number: 5,763,467
[45] Date of Patent: Jun. 9, 1998

[54] HYPOGLYCEMIC HYDROXYUREA DERIVATIVES

[75] Inventors: Steven Wayne Goldstein, Mystic; Ruth Elsbree McDermott, Salem, both of Conn.

[73] Assignee: Pfizer Inc., New York, N.Y.

[21] Appl. No.: 840,179

[22] Filed: Apr. 11, 1997

Related U.S. Application Data

[62] Division of Ser. No. 544,010, Oct. 10, 1995, Pat. No. 5,646,168, which is a division of Ser. No. 391,308, Feb. 17, 1995, Pat. No. 5,463,070, which is a continuation of Ser. No. 279,322, Jul. 22, 1994, abandoned, which is a division of Ser. No. 983,538, filed as PCT/US91/04352, Jun. 26, 1991, Pat. No. 5,334,604, which is a continuation of Ser. No. 572,745, Aug. 23, 1990, abandoned.

[51] Int. Cl.$^6$ ............................................. C07D 413/06
[52] U.S. Cl. ................................... 514/374; 548/235
[58] Field of Search ............................ 548/235; 514/374

[56] References Cited

U.S. PATENT DOCUMENTS

| | | | |
|---|---|---|---|
| 3,437,664 | 4/1969 | Krenzer | 548/132 |
| 3,895,023 | 7/1975 | Sharpe | 548/132 |
| 4,340,605 | 7/1982 | Kawamatsu et al. | 548/183 |
| 4,342,771 | 8/1982 | Schnur | 546/152 |
| 4,367,234 | 1/1983 | Schnur | 548/226 |
| 4,406,910 | 9/1983 | Pilgrim et al. | |
| 4,617,312 | 10/1986 | Schnur | 514/369 |
| 4,703,052 | 10/1987 | Eggler et al. | 514/337 |
| 4,725,610 | 2/1988 | Meguro | 514/369 |
| 4,758,263 | 7/1988 | Krenzer | 548/132 |
| 4,826,990 | 5/1989 | Musser et al. | 548/203 |
| 4,895,953 | 1/1990 | Musser et al. | 548/236 |
| 5,239,080 | 8/1993 | Sohda et al. | 548/236 |
| 5,428,048 | 6/1995 | Malamas et al. | 514/374 |
| 5,459,154 | 10/1995 | Malamas et al. | 514/374 |
| 5,468,760 | 11/1995 | Malamas et al. | 514/374 |
| 5,480,896 | 1/1996 | Malamas | 514/364 |

FOREIGN PATENT DOCUMENTS

| | | |
|---|---|---|
| 0177353 | 4/1986 | European Pat. Off. |
| 0299620 | 1/1989 | European Pat. Off. |
| 89-08650 | 9/1989 | WIPO |
| 89-08651 | 9/1989 | WIPO |
| 92-03425 | 3/1992 | WIPO |

OTHER PUBLICATIONS

Sohda, et al., Chem. Pharm. Bull. Japan, 30, 3580–3600 (1982).

*Primary Examiner*—Donald G. Daus
*Attorney, Agent, or Firm*—Peter C. Richardson; Gregg C. Benson; James T. Jones

[57] ABSTRACT

Certain 1-(benzyl or 5-benzofuranylmethyl)-1-hydroxyurea derivatives are useful as hypoglycemic and hypocholesterolemic agents.

15 Claims, No Drawings

HYPOGLYCEMIC HYDROXYUREA DERIVATIVES

This is a division, of application Ser. No. 08/544,010, filed on Oct. 10, 1995, now U.S. Pat. No. 5,646,168 which is a divisional of application Ser. No. 08/391,308, filed on Feb. 17, 1995, now U.S. Pat. No. 5,463,070, which is a continuation of application Ser. No. 08/279,322, filed Jul. 22, 1994, now abandoned, which is a divisional of application Ser. No. 07/983,538, filed Feb. 22, 1993, now U. S. Pat. No. 5,334,604, which is a National Phase Filing based on PCT/US91/04352, filed internationally on Jun. 26, 1991 as a continuation of U.S. application Ser. No. 07/572,745 filed Aug. 23, 1990, abandoned.

BACKGROUND OF THE INVENTION

The present invention relates to certain compounds of the formulas (I) and (II), depicted below, having utility as hypoglycemic and hypocholesterolemic agents, methods for their use and pharmaceutical compositions containing them, and intermediates useful in their synthesis.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus) requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

Furthermore, atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057–1080].

Schnur, in U.S. Pat. Nos. 4,342,771, 4,367,234 and 4,617, 312, discloses various hypoglycemic oxazolidine-2,4-diones and thiazolidine-2,4-diones substituted at the 5-position with aryl or heteroaryl groups.

Kawamatsu et al., U.S. Pat. No. 4,340,605, disclose hypoglycemic thiazolidine-2,4-dione compounds of the formula

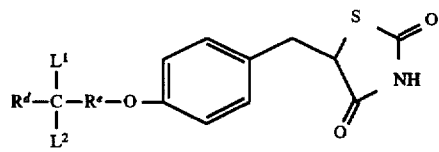

wherein $R^e$ is a bond or lower alkylene and when $R^d$ is an optionally substituted five- or six-membered heterocyclic group including one or two hetero-atoms selected from N, O and S, $L^1$ and $L^2$ may each be defined as hydrogen. See also Sohda et al., Chem. Pharm. Bull. Japan, Vol. 30, pp. 3580–3600 (1982).

Eggler et al., U.S. Pat. No. 4,703,052, disclose hypoglycemic thiazolidinediones of the formula

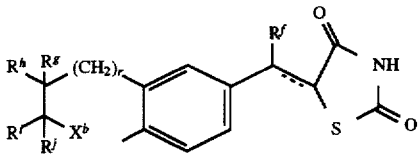

where the dotted line represents an optional bond, $R^f$ is H, methyl or ethyl, $X^b$ is O, S, SO, $SO_2$, $CH_2$, Co, CHOH or $NR^k$, $R^k$ is H or an acyl group and the numerous definitions of $R^g$, $R^h$, $R^i$ and $R^j$ include $R^g$, $R^h$ and $R^i$ as hydrogen or methyl and $R^j$ as optionally substituted phenyl, benzyl, phenethyl or styryl. EP 283,035A and EP 299,620A describe structurally related benzoxazole and benzofuran derivatives as antidiabetic agents.

Clark et al., in published World patent applications WO89/08650, WO89/8651 and WO89/08652 disclose hypoglycemic thiazolidinediones which collectively include compounds of the type:

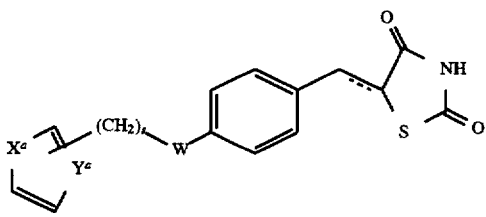

wherein - - - - represents a bond or no bond; W is O, CO, $CH_2$, CHOH, or —CH=CH—; s is 0, 1 or 2; $X^a$ is S, O, $NR^a$, —CH=CH—, —CH=N—or -N=CH—; and $Y^a$ is CH or N.

SUMMARY OF THE INVENTION

The present invention is directed to compounds having the formulas

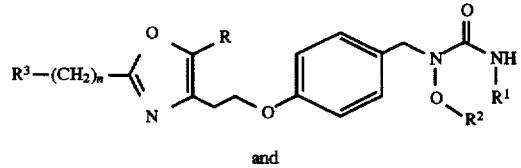

and

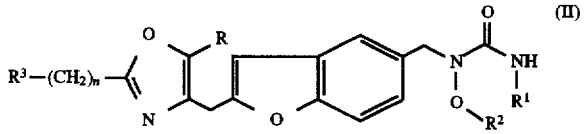

wherein

R is hydrogen or $(C_1-C_3)$alkyl $R^1$ and $R^2$ are taken together and are carbonyl; or $R^1$ and $R^2$ are taken separately, $R^1$ is hydrogen or $R^4$, and $R^2$ is $COR^5$ or $COOR^5$;

R $^3$, $R^4$ and $R^5$ are each independently $(C_1-C_9)$alkyl, $(C_3-C_7)$cycloalkyl, phenyl, naphthyl, furyl, benzofuryl or thienyl or one of said groups mono- or disubstituted with $(C_1-C_3)$alkyl, $(C_1-C_3)$alkoxy, $(C_1-C_3)$alkoxycarbonyl, trifluoromethyl, fluoro or chloro; and n is 0 or 1; and the pharmaceutically-acceptable cationic salts thereof.

In the present compounds, the preferred value of R is methyl; the preferred values of $R^1$ are hydrogen, $(C_1-C_4)$ alkyl or phenyl; the preferred value of $R^2$ is $COOR^5$ where $R^5$ is $(C_1-C_4)$alkyl or phenyl; the preferred values of $R^3$ are $(C_4-C_8)$alkyl, $(C_3-C_6)$cycloalkyl, phenyl (optionally substituted by methyl, methoxy or trifluoromethyl), naphthyl, furyl and benzofuranyl.

The present compounds are generally acidic, such that the expression "pharmaceutically-acceptable cationic salts" is intended to define but not limited to such salts as an alkali metal salt (e.g., Na, K), an alkaline earth salt (e.g., Ca, Mg) or an amine salt (e.g., dicyclohexylamine, diethanolamine, meglumine). Conventional methods are used to prepare such salts.

Also embraced by the present invention are pharmaceutical compositions for use in treating a hyperglycemic mammal or a hypercholesterolemic mammal which comprise a blood glucose lowering amount or a blood cholesterol lowering amount of a compound of formula (I) or (II) and a pharmaceutically-acceptable carrier. The invention further comprises a method of lowering blood glucose in a hyperglycemic mammal which comprises administering to said mammal a blood glucose lowering effective amount of a compound of formula (I) or (II); and a method of lowering blood cholesterol in a hypercholesterolemic mammal which comprises administering to said mammal a blood cholesterol lowering amount of a compound of the formula (I) or (II). The preferred use of the present compounds relates to the treatment of hyperglycemic mammals, especially man.

The present invention is also directed to intermediate compounds of the formulas

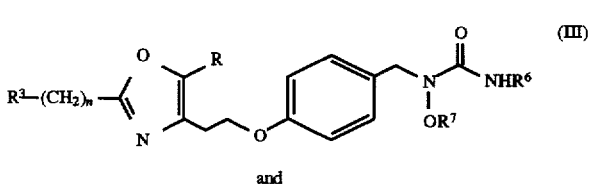

and

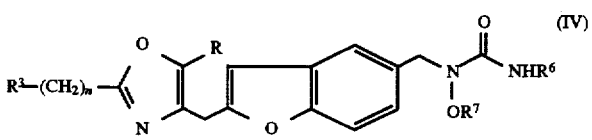

wherein n, R and $R^3$ are as defined above, $R^6$ is hydrogen or independently a value of $R^3$ as defined above, and $R^7$ is hydrogen or a conventional hydroxy protecting group. Useful hydroxy protecting groups include those removable by selective hydrogenation (e.g., benzyl, benzyloxycarbonyl).

DETAILED DESCRIPTION OF THE PRESENT INVENTION

The compounds of the formulas (I) and (II) of the present invention are readily prepared. Those compounds wherein $R^1$ and $R^2$ are taken together and are carbonyl, forming a 1,2,4-oxazolidine-3,5-dione ring, are best prepared from the corresponding precursor of the formula (III) or (IV), wherein each of $R^6$ and $R^7$ are hydrogen, by the action of substantially one molar equivalent of a chloroformate ester (preferably a $(C_1-C_4)$alkyl chloroformate such as ethyl chloroformate) in the presence of excess molar equivalents of a strong base (e.g. 2–3 molar equivalents of 2N NaOH) in a reaction-inert organic solvent (preferably a relatively polar ether such as tetrahydrofuran). The reaction is generally carried out under relatively dilute conditions (e.g. about 1–2% w/v of substrate and organic solvent). Temperature is not critical and will generally be in the range of about 0°–50° C., conveniently ambient temperature so as to avoid the cost of heating or cooling the reaction mixture.

As used above and elsewhere herein, the expression "reaction inert solvent" refers to a solvent which does not interact with starting materials, reagents, intermediates or products in a manner which adversely affects the yield of the desired product.

The same or related reagents (e.g., simple acid chlorides) are used to prepare compounds of the formula (I) and (II) wherein $R^1$ and $R^2$ are taken separately, generally limiting the base and the chloroformate ($R^5OCOCl$) or acid chloride ($R^5COCl$) to substantially one molar equivalent. Solvent and base are not critical. With an aqueous solvent, the preferred bases are NaOH or KOH, while in an organic solvent (e.g., tetrahydrofuran, methylenechloride) a tertiary amine such as triethylamine is generally preferred.

The required hydroxyurea precursors are conveniently prepared by deprotection of protected hydroxyurea of the formula (III) or (IV) wherein $R^7$ is a hydroxy protecting group. The preferred protecting group, which is benzyl, is readily removed by conventional hydrogenolysis over a noble metal catalyst in a reaction-inert solvent. The preferred catalyst is Pd/C using moderate temperatures and pressures. Alternatively, the benzyl group is removed by the action of a large excess of ammonium formate (e.g., 4–5 molar equivalents) under the influence of Pd/C catalyst in a solvent such as ethanol, generally at a somewhat elevated temperature, e.g., in the range of about 30°–70° C.

Another convenient synthesis of present intermediate hydroxyureas is by the action of an isocyanate on the corresponding hydroxylamine:

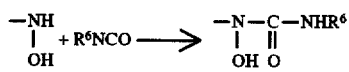

This reaction is generally carried out in a reaction-inert solvent, such as methylene chloride, using substantially molar equivalent amounts of the reagents. The temperature of this reaction is not critical, with temperatures in the range 0°–50° C. generally satisfactory and ambient temperature particularly convenient.

The starting protected hydroxyureas are prepared by multistep methods generally employing organic reaction steps analogous to those known in the art. These are illustrated in Preparations detailed below.

The cationic salts of the present invention are prepared by reacting the acidic form of the present compounds with a base, e.g., NaOH, $Na_2CO_3$, $K_2CO_3$, $Ca(OH)_2$, $NH_3$, dicyclohexylamine, etc. At least one molar equivalent and frequently a molar excess of the base is employed. The free acid and the base are usually combined in a co-solvent from which the desired salt precipitates, or can be otherwise isolated by concentration and/or addition of a non-solvent.

The present compounds of the formulas (I) and (II) are readily adapted to clinical use as hypoglycemic or hypocholesterolemic agents. The activity required for this former clinical use is defined by the test for hypoglycemic effect in ob/ob or db/db mice by the following procedure:

Five to eight week old C57BL/6J-ob/ob or C57BL/K,J-db/db mice (obtained from Jackson Laboratory, Bar Harbor, Maine) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5–50 mg/kg), a positive control (50 mg/kg) of ciglitazone; U.S. Pat. No. 4,467,902; Sohda et al., Chem. Pharm. Bull., vol. 32, pp. 4460–4465, 1984), or vehicle. All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000 ×g at room temperature. The supernatant was analyzed for glucose, for example, by the ABA 200 Bichromatic Analyzer™, using the A-gent™ glucose UV reagent system* (hexokinase method) using 20, 60 and 100 mg/dl standards. Plasma glucose was then calculated by the equation, Plasma glucose (mg/dl)=Sample value×5×1.67=
8.35×Sample value where 5 is the dilution factor and 1.67 is the plasma hematocrit adjustment (assuming the hematocrit is 40%).
™A registered trademark of Abbott Laboratories, Diagnostics Division, 820 Mission Street, So. Pasadena, Calif. 91030.
*A modification of the method of Richterich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) effect the lowering of serum cholesterol levels in mammals.

Female mice (strain C57Br/cd J), obtained from Jackson Laboratories, Bar Harbor, Me., are used at age 8–12 weeks, following 2–4 weeks acclimation having free access to water and standard laboratory chow. Animals are divided randomly into three groups of 6–7 animals. All three groups are placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 18 days; and dosed daily at 9–11 a.m. for the final 5 days by oral gavage, the control group with 5 ml/kg of vehicle (0.1% aqueous methyl cellulose) and the test groups with the compound under study at doses ranging from 0.1 to 10 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbott VP automated analyzer, for HDL cholesterol, LDL and VLDL cholesterol, and total cholesterol. Whether judged on the basis LDL+VLDL cholesterol levels, total cholesterol levels or the ratio of LDL+VLDL/HDL, the compounds of this invention generally show favorable result in lowering cholesterol levels.

The present compounds of the formulas (I) and (II) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts of the compounds. The injectable solutions prepared in this manner can then be administered intravenously, intraperitoneally, subcutaneously, or intramuscularly, with intramuscular administration being preferred in man.

The present invention is illustrated by the following Examples. However, it should be understood that the invention is not limited to the specific details of these examples. Nomenclature used herein is based on Rigaudy and Klesney, IUPAC Nomenclature of Organic Chemistry, 1979 Ed., Pergammon Press, New York, 1979.

EXAMPLE 1

N-carbamoyl-N-ethoxycarbonyloxy-4-[2-(5-methyl-2-phenyl-4-oxazolyl)ethoxy]benzylamine (II; R=methyl, $R^1$=H, $R^2$=$COOR^5$, $R^5$=$C_2H_5$, $R^3$=$C_6H_5$; n=0)

To a 0° C. suspension of the product of preparation I (350 mg, 0.95 mmol) and 2N NaOH (0.47 mL) was added ethyl chloroformate (0.091 mL, 0.95 mmol) and the reaction allowed to warm to room temperature. After stirring for 1 hour, the reaction was diluted with ice water (5 mL) and acidified to pH 2 with 6N HCl. The resultant solid was collected via vacuum filtration and washed with water. Chromatography on silica gel with 2% MeOH/CHCl$_3$ gave the title compound (70 mg, 17%) as a white solid:mp 130°–133° C.

|  |  | C | H | N |
|---|---|---|---|---|
| $C_{23}H_{25}N_3O_6$ | calc | 62.86 | 5.73 | 9.56 |
|  | fnd | 62.44 | 5.54 | 9.26 |

By the same method, the following additional compounds of the formula (II) wherein R is methyl, $R^1$ is hydrogen and $R^2$ is $COOR^5$ were prepared from corresponding hydroxy ureas of the formula (IV) wherein $R^6$ and $R^7$ and are each hydrogen and chloroformate ester ($R^5OCOCl$):

| $R^3$ | n | $R^5$ | Yield (%) | mp (°C.) | C | H | N |
|---|---|---|---|---|---|---|---|
| Ph | 0 | Me | 33 | 153–156 | 60.19 | 5.63 | 9.57[a] (calc) |
|  |  |  |  |  | 60.32 | 5.32 | 9.12 (fnd) |
| Ph | 0 | iBu | 22 | 101–103 | 64.23 | 6.25 | 8.99 |
|  |  |  |  |  | 64.14 | 6.09 | 8.72 |
| Ph | 0 | Ph | 11 | 130–132 | 65.91 | 5.22 | 8.54[b] |
|  |  |  |  |  | 65.90 | 4.90 | 8.32 |
| 2-furyl | 0 | Me | 25 | 119–121 | 57.83 | 5.10 | 10.12 |
|  |  |  |  |  | 57.46 | 5.08 | 9.92 |
| 2-furyl | 0 | Et | 31 | foam |  |  |  |
| 2-furyl | 0 | iBu | 49 | 102–103 | 60.39 | 5.95 | 9.19 |
|  |  |  |  |  | 60.09 | 5.73 | 9.02 |
| 2-furyl | 0 | Ph | 30 | 136–138 | 62.89 | 4.86 | 8.80 |
|  |  |  |  |  | 62.47 | 4.72 | 9.05 |
| 2(OMe)Ph | 0 | Me | 7 | 143–145 |  |  |  |
| 2(OMe)Ph | 0 | Et | 6 | 99–103 | 58.05 | 6.09 | 8.46[c] |
|  |  |  |  |  | 58.38 | 5.80 | 7.82 |
| 4(CF$_3$)Ph | 0 | Me | 21 | 173–174 | 55.59 | 4.49 | 8.52 |
|  |  |  |  |  | 55.64 | 4.32 | 8.22 |
| 4(CF$_3$)Ph | 0 | Et | 19 | 165–168 | 56.80 | 4.77 | 8.28 |
|  |  |  |  |  | 56.65 | 4.65 | 8.10 |
| 4(CF$_3$)Ph | 0 | iBu | 13 | 148–150 | 58.32 | 5.27 | 7.85 |
|  |  |  |  |  | 58.16 | 5.22 | 7.72 |
| 4(CF$_3$)Ph | 0 | Ph | 17 | 173–175 | 59.57 | 4.46 | 7.44[d] |
|  |  |  |  |  | 59.39 | 3.90 | 7.38 |
| Bu | 1 | Me | 18 | 81–84 |  |  |  |
| Bu | 1 | Et | 18 | 93–94 | 60.32 | 7.25 | 9.59[b] |
|  |  |  |  |  | 60.12 | 7.12 | 9.69 |
| Bu | 1 | iBu | 49 | 104–106 | 62.45 | 7.64 | 9.10 |
|  |  |  |  |  | 62.43 | 7.88 | 9.16 |
| cPr | 1 | Me | 37 | 100–103 | 57.61 | 6.41 | 10.08[a] |
|  |  |  |  |  | 57.69 | 5.85 | 9.82 |
| cPr | 1 | Et | 46 | 104–106 |  |  |  |
| cPr | 1 | iBu | 48 | 96–98 | 62.00 | 7.01 | 9.43 |
|  |  |  |  |  | 61.68 | 6.74 | 9.43 |
| cPr | 1 | Ph | 16 | 115–117 | 63.68 | 5.91 | 8.91[e] |
|  |  |  |  |  | 63.36 | 5.47 | 8.84 |
| 2-naphthyl | 0 | Me | 8 | 123–127 |  |  |  |
| 2-bzfuryl | 0 | Me | 20 | 149–151 | 60.75 | 5.10 | 8.86[d] |
|  |  |  |  |  | 60.69 | 4.71 | 8.68 |
| 2-bzfuryl | 0 | Et | 45 | 130–132 | 60.90 | 5.42 | 8.52[a] |
|  |  |  |  |  | 60.57 | 5.01 | 8.25 |

[a] 0.75 hydrate
[b] 0.25 hydrate
[c] 1.5 hydrate
[d] 0.50 hydrate
[e] 0.33 hydrate
Ph = phenyl
Me = methyl
Et = ethyl
Bu = butyl
iBu = isobutyl
cPr = cyclopropyl
bzfuryl = benzofuranyl

EXAMPLE 2

5-[(1,2,4-Oxadiazolidine-3,5-dion-2-yl)methyl]-2-[(5-methyl-2-(4-methylphenyl)-4-oxazolyl)-methyl]benzofuran

[I, R=$CH_3$, $R^1$+$R^2$=CO, $R^3$=4($CH_3$)$C_6H_4$, n=0]

To a 0° C. suspension of the product of Preparation Y (1.39 g, 3.55 mmol), THF (90 mL) and 2N NaOH (5.33 mL, 10.7 mmol) was added ethyl chloroformate (0.35 mL, 3.69 mmol) in a dropwise fashion. After stirring at room temperature the reaction was cooled to 0° C., diluted with water (200 mL) and adjusted to pH 2 with 6N HCl. The THF was removed with a stream of nitrogen and the resultant solid was collected by vacuum filtration. Chromatography on silica gel utilizing a gradient elution of $CHCl_3$ to 2% MeOH/$CHCl_3$ gave the title compound (950 mg, 64%) as a yellow solid: mp 201°–203° C.

|  |  | C | H | N |
|---|---|---|---|---|
| $C_{22}H_{19}N_3O_5$ | calc | 66.18 | 4.59 | 10.07 |
|  | fnd | 66.15 | 4.49 | 9.70 |

By the same method, the following additional compounds were prepared from the corresponding hydroxyureas:

5-[(1,2,4-Oxadiazolidine-3,5-dion-2-yl)methyl]-2-[(5-methyl-2-(2-furyl)-4-oxazolyl)methyl]benzofuran; 74% yield; mp 191°–193° C.

5-[(1,2,4-Oxadiazolidine-3,5-dion-2-yl)methyl]-2-[(5-methyl-2-phenyl-4-oxazolyl)methyl]benzofuran; 27% yield; mp 89°–91° C.

2-[[4-(2-(5-methyl-2-cyclopropylmethyl-4-oxazolyl)ethoxy)phenyl]methyl]-1,2,4-oxazolidine-3,5-dione; 52% yield; mp 139°–141° C.

Substituting an equivalent amount of methyl chloroformate for ethyl chloroformate, the same method was used to prepare the following additional compounds from the corresponding hydroxyureas:

2-[[4-(2-(5-methyl-2-(4-methoxyphenyl)-4-oxazolyl)ethoxy)phenyl]methyl]-1,2,4-oxazolidine-3,5-dione; 9% yield; mp 143°–145° C.

2-[[4-(2-(5-methyl-2-(2-furyl)-4-oxazolyl)ethoxy)phenyl]methyl]-1,2,4-oxazolidine-3,5-dione; 9% yield; mp 180°–183° C.

2-[[4-(2-(5-methyl-2-(2-naphthyl)-4-oxazolyl)ethoxy)phenyl]methyl]1,2,4-oxazolidine-3,5-dione; 15% yield; mp 145°–150° C.

Substituting an equivalent amount of methyl chloroformate for ethyl chloroformate and equivalent triethylamine for NaOH, the same method was used to prepare the following additional compound from the corresponding hydroxyurea:

2-[[4-(2-(5-methyl-2-phenyl-4-oxazolyl)ethoxy)phenyl]methyl]-1,2,4-oxazolidine-3,5-dione; 19% yield; mp 148°–150° C.

EXAMPLE 3

N-(Methoxycarbonyloxy)-N-(methylaminocarbonyl)-4-[2-(5-methyl-2-phenyl-4-oxazolyl)ethoxy]benzylamine To a suspension of the product of Preparation J (185 mg, 0.49 mmol) in $CH_2Cl_2$ (4 mL) was added triethylamine (0.070 mL, 0.53 mmol). After cooling to 0° C., methyl chloroformate (0.041 mL, 0.53 mmol) was added and the reaction stirred for 1.5 hours at 10° C. It was then diluted with $CH_2Cl_2$ (20 mL), washed with water (2×10 mL), dried ($Na_2SO_4$), filtered and concentrated. Chromatography on silica gel eluting with 1/3 ethyl acetate:hexanes gave the title compound (60 mg, 29%) as a white solid: mp 134°–135° C.

|  |  | C | H | N |
|---|---|---|---|---|
| $C_{23}H_{25}N_2O_6 \cdot 0.25\ H_2O$ | calc | 62.22 | 5.79 | 9.47 |
|  |  | 62.29 | 5.72 | 8.85 |

By the same method, the following additional compounds were prepared from the corresponding hydroxyureas:

N-(ethoxycarbonylmethylaminocarbonyl)-N-(methoxycarbonyloxy)-4-[2-(5-methyl-2-phenyl-4-oxazolyl)ethoxy]benzylamine; 58% yield; mp 107°–108° C.

N-[(1-methylethyl)aminocarbonyl]-N-(methoxycarbonyloxy)-4-[2-(5-methyl-2-phenyl-4-oxazolyl)ethoxy]benzylamine; 52% yield; mp 111°–113° C.

By the same method, N-(methoxycarbonyloxy)-N-(phenylaminocarbonyl)-4-[2-(5-methyl-2-phenyl-4-oxazolyl)ethoxy]benzylamine is prepared from the corresponding phenyl-hydroxyurea of Preparation J.

PREPARATION A

Methyl 3-Carboxy-3-(2-furoylamino)propionate

To a 0° C. soluton of beta-methyl aspartate hydrochloride (100 g, 0.545 mol), $CH_2Cl_2$ (1 L) and triethylamine (167 mL, 1.2 mol) was added a solution of $CH_2Cl_2$ (100 mL) and furoyl chloride (71.1 g, 0.545 mol) in a dropwise fashion over 1 hour. The reaction was then stirred for 1 hour at room temperature, quenched by the addition of water (500 mL) and adjusted to pH 2 with conc. HCl. The aqueous layer was separated and extracted with $CH_2Cl_2$ (250 mL). The combined organic layers were dried ($MgSO_4$), filtered and evaporated to give a yellow oil (130 g, 99%).

Also prepared by this method were methyl 3-carboxy-3-(acylamino)propionate esters as follows:

| Acyl Group | Yield(%) | mp(°C.) |
|---|---|---|
| benzoyl | 41 | 148–150 |
| 2(MeO)$C_6H_4$CO | 100 | (oil) |
| 4($CF_3$)$C_6H_4$CO | 98 (foam) |
| n-$C_5H_{11}$CO | 100 | (oil) |
| (c-$C_3H_5$)$CH_2$CO | 11 | (oil) |
| 2-benzofuroyl | 86 | (foam) |
| 2-naphthoyl | 62 | 122–135 |

PREPARATION B

Methyl 3-(2-Furoylamino)-4-oxopentanoate

To a solution of the product of Preparation A (126 g, 0.522 mol) in pyridine (273 mL) was added acetic anhydride (345 mL) and dimethylaminopyridine (3.5 g). The reaction was heated to 93° C. for 2.5 hours, removed from the oil bath and then water (220 mL) was cautiously added in small increments. The reaction was then heated for an additional 20 minutes at 90° C., cooled to room temperature and diluted with water (1 L). This was then extracted with ethyl acetate (3×1 L) and the combined organic layers washed with 10% HCl until the washings were acidic. The organic layer was then washed with water, cautiously with 5% $NaHCO_3$ solution (2×500 mL) and then brine (500 mL). The solution was dried ($MgSO_4$), filtered and concentrated to give a brown oil (74.2 g, 59%).

Also prepared by this method were the following methyl 3-(acylamino)-4-oxopentanoate esters:

| Acyl Group | Yield(%) | mp(°C.) |
|---|---|---|
| benzoyl | 43 | (oil) |
| 2(OMe)$C_6H_4$CO | 93 | (oil) |
| 4($CF_3$)$C_6H_4$CO | 70 | 114–119 |
| n-$C_5H_{11}$CO | 99 | (oil) |
| (c-$C_3H_5$)$CH_2$CO | 53 | (oil) |

-continued

| Acyl Group | Yield(%) | mp(°C.) |
|---|---|---|
| 2-benzofuroyl | 70 | (oil) |
| 2-naphthoyl | 78 | 82–84 |

PREPARATION C

Methyl 2-(5-Methyl-2-(2-furyl)-4-oxazolyl)acetate

To a solution of the product of Preparation B (73 g, 0.305 mol) and toluene (360 mL) was added $POCl_3$ (120 mL) and the solution heated to reflux for 3 hours. The bulk of the solvent was distilled off and the residue was added cautiously to 560 mL of ice water. The pH was adjusted to pH 7 with solid $NaHCO_3$ and the aqueous was extracted with ethyl acetate (2×1 L). The combined organic layers were dried ($MgSO_4$) filtered and concentrated to give the crude product. This was purified by silica gel chromatography with ethyl acetate/hexanes as eluent to afford the title compound as an oil (27.2 g, 40%).

Also prepared by this method were methyl 2-(5-methyl-2-substituted-4-oxazolyl)acetate esters as follows:

| Substituent | Yield(%) | mp(°C.) |
|---|---|---|
| phenyl | 79 | oil |
| 2(OMe)$C_6H_4$ | 76 | <50 |
| 4(CF$_3$)$C_6H_4$ | 66 | 75–80 |
| n-$C_5H_{11}$ | 92 | (oil) |
| (c-$C_3H_5$)$CH_2$ | 81 | (oil) |
| 2-benzofuryl | 75 | 103–104 |
| 2-naphthyl | 60 | (oil) |

PREPARATION D 2-(5-Methyl-2-(2-furyl)-4-oxazolyl)ethanol

To a suspension of lithium aluminum hydride (4.7 g) in dry THF (82 mL) at 0° C. was added a solution of the product of Preparation C (27.2 g, 123 mmol) in THF (82 mL) over 1 hour. The solution was stirred for 1 hour at room temperature, cooled to 0° C. and then quenched by the careful sequential addition of water (5 mL), 15% NaOH (5 mL) and finally water (15 mL). The crude reaction mixture was filtered through celite, and the residual aluminum salts washed with ether (250 mL) The combined organic layers were dried ($MgSO_4$), filtered and concentrated to give the title compound as an oil.

Also prepared by this method were 2-(5-methyl-2-substituted-4-oxazolyl)ethanol derivatives as follows:

| Substituent | Yield(%) | mp(°C.) |
|---|---|---|
| phenyl | 69 | 48–50 |
| 2(OMe)$C_6H_4$ | 84 | 88–91 |
| 4(CF$_3$)$C_6H_4$ | 78 | 63–67 |
| n-$C_5H_{11}$ | 45 | (oil) |
| (c-$C_3H_5$)$CH_2$ | 57 | (oil) |
| 2-benzofuryl | 81 | 71–74 |
| 2-naphthyl | 67 | 74–79 |

*EP 0 177 353 reports 73–74° C.

PREPARATION E

4-[2-(5-Methyl-2-(2-furyl)-4-oxazolyl)ethoxy]benzonitrile

To a solution of the product of preparation D (18.4 g, 95.7 mmol), 4-fluorobenzonitrile (17.4 g, 144 mmol) and THF (195 mL) at 0° C. was added sodium hydride (60% in oil, 4.60 g, 115 mmol) in small portions. The reaction was stirred at room temperature overnight and poured into ice water (1.5 L) and adjusted to pH 3 with acetic acid. The resultant solids were collected by vacuum filtration and dissolved in $CH_2Cl_2$. The organic solution was dried ($MgSO_4$), filtered and concentrated to give the crude product. Recrystallization from methanol gave the title compound (17.6 g, 62%) as yellow needles: mp 105°–108° C.

Also prepared by this method were 4-[2-(5-methyl-2-substituted-4-oxazolyl)ethoxy]benzonitrile derivatives as follows:

| Substituent | Yield(%) | mp(°C.) |
|---|---|---|
| phenyl | 78 | 100–102* |
| 2(OMe)$C_6H_4$ | 99 | 81–83 |
| 4(CF$_3$)$C_6H_4$ | 100 | 103–108 |
| n-$C_5H_{11}$ | 51 | (oil) |
| (c-$C_3H_5$)$CH_2$ | 96 | (oil) |
| 2-benzofuryl | 100 | 125–127 |
| 2-naphthyl | 82 | 132–135 |

*EP 0 177 353 reports 119–120° C.

PREPARATION F

4-[2-(5-Methyl-2-phenyl-4-oxazolyl)ethoxy]benzaldehyde

A solution of the phenyl product from Preparation E (3.5 g, 11.5 mmol), 75% formic acid (50 mL) and Raney Nickel (3.5 g) was heated to reflux for 3 hours. After cooling to room temperature the reaction was filtered through celite and the residual solids washed with ethyl acetate (200 mL). After evaporation of all of the combined filtrates, water (100 mL) was added and the resulting suspension extracted with ethyl acetate (3×100 mL). The combined organic layers were washed with 5% $NaHCO_3$ (2×100 mL), dried ($MgSO_4$), filtered and concentrated to give a yellow solid. The title compound was isolated in two fractions (3.46 g, 98%) following trituration with hexanes: mp 70°–73° C. (lit. 82°–84° C.; EP 0 177 353).

Also prepared by this method were 4-[2-(5-methyl-2-substituted-4-oxazolyl)ethoxy]benzaldehyde derivatives as follows:

| Substituent | Yield(%) | mp(°C.) |
|---|---|---|
| 2-furyl | quant | 63–67 |
| 2(OMe)$C_6H_4$ | 99 | (crude solid) |
| 4(CF$_3$)$C_6H_4$ | 97 | 55–80 |
| n-$C_5H_{11}$ | 100 | (oil) |
| (c-$C_3H_5$)$CH_2$ | 100 | (oil) |
| 2-benzofuryl | 58 | 109–116 |
| 2-naphthyl | 88 | 95–101 |

PREPARATION G

4-[2-(5-Methyl-2-phenyl-4-oxazolyl)ethoxybenzaldoxime

To a solution of the product from Preparation F (4.00 g, 13.0 mmol) hydroxylamine hydrochloride (1.36 g, 19.6 mmol) in ethanol (50 mL) was added pyridine (2.6 mL). The reaction was heated to reflux for 1.5 hours, cooled to room temperature and poured into a mixture of ethyl acetate (400 mL) and water (100 mL). The organic layer was washed with water (100 mL), brine (100 mL), dried (Na₂SO₄), filtered and concentrated to give the product (4.00 g, 96%) as a tan solid: mp 149°–151° C.

Also prepared by this method were 4-[2-(5-methyl-2-substituted-4-oxazolyl)ethoxy]benzaldoximes as follows:

| Substituent | Yield(%) | mp(°C.) |
|---|---|---|
| 2-furyl | 92 | 171–173 |
| 2(OMe)C₆H₄ | 80 | 146–149 |
| 4(CF₃)C₆H₄ | 94 | 123–128 |
| n-C₅H₁₁ | 99 | 93–97 |
| (c-C₃H₅)CH₂ | 94 | 133–135 |

PREPARATION H

N-[4-[2-(5-Methyl-2-phenyl-4-oxazolyl)ethoxy]benzyl]hydroxylamine

To a suspension of the product of Preparation G (4.03 g, 12.5 mmol) in hot methanol (280 mL) was added sodium cyanoborohydride (3.93 g, 62.5 mmol) and a few crystals of methyl orange. A solution of methanol/conc. HCl (1:1) was added in a dropwise fashion until the reaction mixture remained red-orange and heating was continued at 50° C. for 1.5 hours. The reaction was cooled to 0° C., adjusted to pH 9 with 6N NaOH and evaporated to give a yellow residue. This was then dissolved in ethyl acetate (800 mL) and washed with water (200 mL) and brine (2×200 mL). The organic solution was dried (Na₂SO₄), filtered and concentrated to give the product (3.90 g, 97%) as a solid: mp 99°–102° C.

Also prepared by this method were N-[4-[2-(5-methyl-2-substituted-4-oxazolyl)ethoxy]benzyl]hydroxylamine derivatives as follows:

| Substituent | Yield(%) | mp(°C.) |
|---|---|---|
| 2-furyl | 84 | 113–118 |
| 2(OMe)C₆H₄ | 100 | (oil) |
| 4(CF₃)C₆H₄ | 94 | 91–96 |
| n-C₅H₁₁ | 91 | (oil) |
| (c-C₃H₅)CH₂ | 100 | (oil) |

PREPARATION I

1-[4-[2-(5-Methyl-2-phenyl-4-oxazolyl)ethoxy]benzyl]-1-hydroxyurea

To a suspension of the product of Preparation H (1.08 g, 3.0 mmol) and a mixture of acetic acid (1.5 mL) and water (3 mL) at 35° C. was added a solution of potassium cyanate (0.52 g, 6 mmol) in water (3 mL), also at 35° C. After stirring for 10 minutes at 35° C. and then 1 hour at room temperature, an additional portion of potassium cyanate (0.52 g, 6 mmol) in water (3 mL) was added. After stirring for 2 hours at room temperature, the reaction was cooled to 0° C. and the solids were collected by vacuum filtration. This was then dissolved in CHCl₃, the water separated and the organic layer dried (Na₂SO₄), filtered and concentrated to give the crude product. Chromatography on silica gel eluting with MeOH/CHCl₃ gave the title compound (703 mg, 67%) as a white solid: mp 148°–150° C.

Also prepared by this method were 1-[4-[2-(5-methyl-2-substituted-4-oxazolyl)ethoxy]benzyl]-1 hydroxyurea derivatives as follows:

| Substituent | Yield(%) | mp(°C.) |
|---|---|---|
| 2-furyl | 52 | 155–157 |
| 2(OMe)C₆H₄ | 40 | 116–120 |
| 4(CF₃)C₆H₄ | 40 | 115–120 |
| n-C₅H₁₁ | 42 | 98–101 |
| (c-C₃H₅)CH₂ | 42 | (foam) |

PREPARATION J

1-Hydroxy-1-[4-[2-(5-Methyl-2-phenyl-4-oxazolyl)ethoxy]benzyl]-3-methylurea

To a solution of the product of Preparation H (324 mg, 1.00 mmol) and CH₂Cl₂ (2 mL) was added methyl isocyanate (0.059 mL, 1.0 mmol). After 30 minutes the solvent was removed and the resultant solid was triturated with ether (2×5 mL) to give the title compound (267 mg, 70%) as a white solid: mp 139°–144° C.

| | | C | H | N |
|---|---|---|---|---|
| C₂₁H₂₃N₃O₄·0.75 H₂O | calc | 63.86 | 6.25 | 10.64 |
| | fnd | 63.83 | 5.76 | 10.47 |

By substituting methyl isocyanate with a molar equivalent of the appropriate isocyanate, this method was used to prepare additional 1-hydroxy-1-[4-[2-(5-methyl-2-phenyl-4-oxazolyl)ethoxy]benzyl]3-substituted-urea derivatives as follows:

| Substituent | Yield(%) | mp(°C.) |
|---|---|---|
| (CH₃)₂CH | 53 | 89–93 |
| phenyl | 53 | 166–168 |
| EtO₂CCH₂ | 69 | 139–141 |

PREPARATION K

Diethyl 2-((4-Methylbenzoyl) amino) propandioate

To a suspension of diethyl aminomalonate hydrochloride (20.95 g, 97.02 mmol) and dry CH₂Cl₂ (180 mL) was added triethylamine (29.7 mL, 213 mmol). After cooling to 0° C., a solution of p-toluoyl chloride (15 g, 97 mmol) and CH₂Cl₂ (25 mL) was added at a rate such that the reaction temperature remained less than 5° C. The reaction was stirred at room temperature for 1 hour, cooled to 0° C. and quenched with water (90 mL). The organic layer was separated and washed with water (2×100 mL), 10% HCl (2×100 mL), water (2×100 mL) and brine (100 mL). The resultant solution was dried (Na₂SO₄), filtered and concentrated to give the title compound (26.8 g, 94%) as a white solid: mp 98°–99° C.

Also prepared by this method was diethyl 2-((2-furoyl)amino)propandioate; 99% yield; mp 55°–59° C.

PREPARATION L

Ethyl 2-((4-Methylbenxoyl)amino-2-ethoxycarbonyl-4-pentynoate

Sodium hydride (3.7 g, 60% in oil, 92.5 mmol) was placed in a reaction vessel and washed with hexanes (4×10 mL) and then diluted with THF (400 mL). A solution of the product of Preparation K (25 g, 85.2 mmol) and THF (240 mL) was added at such a rate that the reaction temperature was <25° C. After the addition was complete the reaction was stirred at room temperature for 5 minutes and propargyl bromide (10.0 mL, 80% in toluene, 90.5 mmol) was added in one portion and the reaction stirred for 5 days. The reaction was concentrated to about 100 mL and then quenched into saturated ammonium chloride (500 mL). This was extracted with ethyl acetate (2×500 mL) and the combined organic layers were washed with water (200 mL) and brine (200 mL). The solution was dried ($Na_2SO_4$) and concentrated to give an oil (20.7 g, 73%). Trituration of the oil with hexanes gave white solids: mp 70°–73° C.

Also prepared by this method was ethyl 2-((2-furoyl)amino)-2-ethoxycarbonyl-4-pentynoate; 88% yield; mp 90°–93° C.

PREPARATION M 2-((4-Methylbenzoyl)amino)-4-pentynoic Acid

To a solution of the product of Preparation L (20.1 g, 60.7 mmol) and methanol (715 mL) was added a 10% KOH in water solution over 30 minutes. After stirring overnight, the methanol was removed under reduced pressure and the resultant amber solution cooled to 0° C. and diluted with water (750 mL). The pH was adjusted to pH 1 with 6N HCl and extracted with ethyl acetate (2×800 mL). The combined organic layers were washed with brine (200 mL), dried ($Na_2SO_4$) filtered and concentrated to give an amber oil.

This was suspended in xylenes (400 mL) and heated to 138° C. for 1 hour (gas evolution seen) The reaction was cooled in ice and the precipitated tan material was collected by vacuum filtration (13.6 g, 97%) to give the title compound: mp 140°–141° C.

Also prepared by this method was 2-((2-furoyl)-amino-4-pentynoic acid; 88% yield; mp 106°–110° C.

PREPARATION N 3-((4-Methylbenzoyl)amino)-5-hexyn-2-one

To a solution of the product of Preparation M (13.6 g, 58.8 mmol) and 4-dimethylamino pyridine (355 mg) in pyridine (31 mL) was added acetic anhydride (39 mL) and the dark reaction was heated at 93° C. for 1 hour. After cooling to room temperature, water (26 mL) was cautiously added through the top of the condenser and the reaction reheated to 90° C. for 20 minutes. The reaction was cooled to room temperature, diluted with water (500 mL) and extracted with ethyl acetate (2×400 mL). The combined organic layers were washed with water (200 mL), 10% HCl (3×100 mL) and 5% $NaHCO_3$ (3×100 mL). The resulting solution was dried ($Na_2So_4$), filtered and concentrated to give a brown oil which was triturated with hexanes to give the title compound (13.2 g, 98%) as a brown solid: mp 84°–87OC.

Also prepared by this method was 3-((2-furoyl)-amino)-5-hexyn-2-one; 79% yield; mp 65°–67° C.

PREPARATION O 2-(4-Methylphenyl)-4-(2-propynyl)-5-methyloxazole

To a solution of the product of Preparation N (1.00 g, 4.36 mmol) in toluene (5 mL) was added $POCl_3$ (1.7 mL) and the reaction heated to reflux for 3 hours. The solvent was removed by distillation, and the residue was added to ice water (20 mL). The solution was adjusted to pH 7 with sodium carbonate and extracted with ethyl acetate (2×25 mL). The combined organic layers were washed with brine (20 mL), dried ($Na_2SO_4$), filtered and concentrated. This was then chromatographed on silica gel with 10/1 hexanes:ether as eluent to afford the title compound (627 mg, 65%) as a yellow solid: mp 65°–68° C.

Also prepared by this method was 2-(2-furyl)-4-(2-propynyl)-5-methyloxazole; 64% yield; oil.

PREPARATION P

5-Formyl-2-[(5-methyl-2-(4-methylphenyl)-4-oxazolyl)methyl]benzofuran

A suspension of $Cu_{2O}$ (3.22 g, 22.5 mmol), the product of Preparation O (7.82 g, 37.0 mmol), 3-iodo-4-hydroxybenzaldehyde (7.65 g, 30.8 mmol) and bis(triphenylphosphine)palladium dichloride (169 mg, 0.24 mmol) in pyridine (100 mL) was heated to reflux for 20 hours. After cooling to room temperature, the reaction was filtered through celite and concentrated to a dark mass. This was then chromatographed on florisil with 9/1 hexanes:ethylacetate as the eluent to give the title compound (6.47 g, 63%) as a yellow solid: mp 126°–130° C.

Also prepared by this method was 5-formyl-2-[(5-methyl-2-(2-furyl)-4-oxazolyl)methyl]benzofuran; 89% yield; mp 125°–126° C.

PREPARATION Q 2-(2-Phenyl-5-methyloxazol-4-ylcarbonyl)-5-bromobenzofuran

To a slurry of 294 g of 5-bromosalicylaldehyde in 3 liters of dry ethanol was added 79.06 g of sodium methoxide and the mixture allowed to stir for 20 minutes. To the resulting yellow slurry was added 410 g of 2-phenyl-4-bromoacetyl-5-methyloxazole and the slurry heated to 780° C. for 2 hours. An additional 250 mg of sodium methoxide was added and heating continued overnight under a nitrogen atmosphere. The reaction was cooled and the solids filtered and washed with ethanol, 393 g, mp 212°–213° C.

Also prepared by this method were 2-(2-substituted-5-methyloxazol-4-ylcarbonyl)-5-bromobenzofuran derivatives as follows:

| Substituent | mp(°C.) |
| --- | --- |
| 2-naphthyl | 231—234 |
| 4($CH_3$)$C_6H_4$ | — |
| 3($CH_3$)$C_6H_4$ | 173–178 |
| n$C_6H_{11}$ | — |

PREPARATION R

2-[1-(2-Phenyl-5-methyloxazol-4-yl)-1hydroxymethyl]-5-bromobenzofuran

To a slurry of 265.44 g of the product of Preparation Q in 2.1 liters of tetrahydrofuran was added 2.5 liters of absolute methanol and the slurry cooled in an ice bath. Sodium borohydride (26.3 g) was added in four portions over a period of 15 minutes. After stirring in the cold for 30 minutes, the reaction mixture was allowed to warm to room temperature. After 1 hour the solvent was removed in vacuo and the residue treated with 3 liters of water. The solids were filtered, washed with water and dried in vacuo, 221.48 g, mp 152°–154° C.

Also prepared by this method were 2-[1-(2-substituted-5-methyloxazol-4-yl)-1-hydroxymethyl]-5-bromobenzofuran derivatives as follows:

| Substituent | mp(°C.) |
|---|---|
| 2-naphthyl | 189—191 |
| 4(CH$_3$)C$_6$H$_4$ | — |
| 3(CH$_3$)C$_6$H$_4$ | 133–136 |
| nC$_6$H$_{11}$ | — |

PREPARATION S

2-[(2-Phenyl-5-methyloxazol-4-yl)methyl]-5-bromobenzofuran

Trifluoroacetic acid (7 ml) was added to 1.35 g of the product of Preparation R under a nitrogen atmosphere followed by the addition of 817 mg of triethylsilane and the reaction mixture stirred for 1 hour at 0° C.

The reaction was diluted with 125 ml of ethyl acetate and the organic phase washed with water (1×50 ml), 1M sodium hydroxide solution (1×50 ml), water (1×50 ml) and a brine solution (2×50 ml). The organic phase was dried and concentrated in vacuo to give the crude product, which was chromatographed on silica gel (ethyl acetate-hexane; 10%–90%; v:v), 1.28 g, mp 98°–100° C.

Also prepared by this method were 2-[(2-substituted-5-methyloxazol-4-yl)methyl]-5-bromobenzofuran derivatives as follows:

| Substituent | mp(°C.) |
|---|---|
| 2-naphthyl | 143—145 |
| 4(CH$_3$)C$_6$H$_4$ | — |
| 3(CH$_3$)C$_6$H$_4$ | 88–90 |
| nC$_6$H$_{11}$ | (oil) |

PREPARATION T

2-(2-Phenyl-5-methyloxazol-4-ylmethyl)-5-cyanobenzofuran

A mixture of 1.28 g of the product of Preparation S and 623 mg of cuprous cyanide was treated with 10 ml of dimethylformamide and the yellow slurry heated under a nitrogen atmosphere overnight at 150° C. The mixture was cooled and poured into 15 ml of concentrated ammonium hydroxide diluted with 5 ml of water. An additional 25 ml of ammonium hydroxide was added and the mixture extracted with 200 ml of ethyl acetate. The organic phase was separated, washed with water (3×75 ml) and a brine solution (2×50 ml) and dried over sodium sulfate. The residue resulting from removal of the solvent in vacuo was chromatographed on 100 g of silica gel (ethyl acetate-hexane; 20%–80%; v:v) to give 626 mg of product, mp 139°–140° C.

Also prepared by this method were 2-(2-substituted-5-methyloxazol-4-ylmethyl)-5-cyanobenzofuran derivatives as follows:

| Substituent | mp(°C.) |
|---|---|
| 2-naphthyl | 175—176 |
| 4(CH$_3$)C$_6$H$_4$ | — |
| 3(CH$_3$)C$_6$H$_4$ | 125–126 |
| nC$_6$H$_{11}$ | 85–87 |

PREPARATION U

5-Formyl-2-[(2-phenyl-5-methyl-4-oxazolyl)methyl]benzofuran

A mixture of 620 mg of the product of Preparation T and 620 mg of a 50% aluminum-nickel alloy in 20 ml of 70% formic acid was heated to reflux for 2 hours. The reaction was cooled and the solids filtered. The filtrate was extracted with 200 ml of ethyl acetate and the extract washed with water (2×75 ml), 1N sodium hydroxide solution, water (2×75 ml) and a brine solution (1×50 ml). The extract was dried over sodium sulfate and concentrated to give 544 mg of the desired product, m.p. 116°–118° C.

Also prepared by this method were 5-formyl-2-[(2-derivatives-5-methyl-4-oxazolylmethyl]benzofuran derivatives as follows:

| Substituent | mp(°C.) |
|---|---|
| 2-naphthyl | 153—155 |
| 4(CH$_3$)C$_6$H$_4$ | 128–129 |
| 3(CH$_3$)C$_6$H$_4$ | — |
| nC$_6$H$_{11}$ | (oil) |

PREPARATION V

2-[(5-Methyl-2-(4-methylphenyl)-4-oxazolyl)methyl]-5-(hydroxymethyl) benzofuran A suspension of the product of Preparation P (8.74 g, 26.4 mmol) in ethanol (260 mL) was heated until all of the solid was dissolved. The solution was cooled until just before a precipitate formed and NaBH$_4$ (874 mg, 23 mmol) was added in four equal portions. The reaction was stirred at room temperature for 1 hour and then concentrated. The resultant solid was washed with water and the residue collected by vacuum filtration to give the title compound (7.99 g, 90%) as a tan solid: mp 156°–160° C.

Also prepared by this method were 2-[(5-methyl-2-substituted-4-oxazolyl)methyl-5-(hydroxymethyl) benzofuran derivatives as follows:

| Substituent | Yield(%) | mp(°C.) |
|---|---|---|
| 2-furyl | 81 | 123–125 |
| phenyl | 60 | 145–147 |

Analogous compounds having a 3-methylphenyl or n-hexyl substituent in place of the 4-methylphenyl substituent are prepared in like manner.

Also prepared by this method were 4-[2-(5-methyl-2-(2-substituted-5-methyl-4-oxazolyl) ethoxy]benzyl alcohols as follows:

| Substituent | Yield(%) | mp(°C.) |
|---|---|---|
| 2-naphthyl | 99 | (solid) |
| 2-benzofuryl | 86 | 122–123 |

PREPARATION W

5-Chloromethyl-2-[(5-methyl-2-(4-methyl-phenyl)-4-oxazolyl)methyl]benzofuran

To a suspension of the product of Preparation V (7.7 g, 23 mmol) in dry DMF (115 mL) at 0° C. was added triphenylphosphine (7.3 g, 28 mmol) and CCl$_4$ (4.8 mL, 51 mmol). The reaction was allowed to stir overnight at room temperature and then poured into ice water (500 mL). This was extracted with ethyl acetate (3×300 mL) and the combined organic layers washed with water (2×300 mL) and brine (200 mL), dried (Na$_2$SO$_4$), filtered and concentrated to give the crude product. Chromatographic purification silica gel with 2:1 hexanes/ether as eluent afforded the title compound (6.53 g, 80%) as a yellow solid: mp 145°–146° C.

Also prepared by this method were 5-chloromethyl-2-[(5-methyl-2-substituted-4-oxazolyl)methyl]benzofuran derivatives as follows:

| Substituent | Yield(%) | mp(°C.) |
|---|---|---|
| 2-furyl | 100 | 110–113 |
| phenyl | 63 | 109–111 | and 4-[2-(5-methyl-2-substituted-4-oxazolyl)ethoxy]benzyl chloride derivatives as follows:

| Substituent | Yield(%) | mp(°C.) |
|---|---|---|
| 2-naphthyl | 50 | 124–125 |
| 2-benzofuryl | 57 | 119–121 |

PREPARATION X

1-Benzyloxy-1-[2-[(5-methyl-2-(4-methylphenyl)-4-oxazolyl)methyl]-5-benzofuranyl]urea Sodium hydride (1.40 g, 60% in oil, 35.1 mmol) was washed with hexanes (3×20 mL) and then diluted with dry DMF (30 mL). A solution of O-benzylhydroxyurea (15.4 g, 92.8 mmol) and DMF (52 mL) was added and then heated to 100OC. for 15 minutes and then cooled to room temperature. A solution of the product of Preparation W (6.53 g, 18.6 mmol) and DMF (50 mL) was added and the reaction heated to 110OC. for 6 hours. After cooling to 0° C., the reaction was quenched into 500 mL water and extracted with ethyl acetate (3×300 mL). The combined organic layers were washed with water (3×150 mL), brine (200 mL), dried (Na$_2$SO$_4$), filtered and concentrated to give a yellow solid. Chromatography on florisil with gradient eluent of 1/8 ethyl acetate:hexanes to ethyl acetate afforded the title compound (5.08 g, 57%) as a yellow solid: mp 77°–80° C.

Also prepared by this method were 1-benzyloxy-1-[2-[(5-methyl-2-substituted-4-oxazolyl)methyl]-5-benzofuranyl]urea derivatives as follows:

| Substituent | Yield(%) | mp(°C.) |
|---|---|---|
| 2-furyl | 43 | 129–132 |
| phenyl | 43 | 124–128 | and 1-benzyloxy-1-[4-(2-(5-methyl-2-substituted-4-oxazolyl) ethoxy)benzyl]urea derivatives as follows:

| Substituent | Yield(%) | mp(°C.) |
|---|---|---|
| 2-naphthyl | 48 | (foam) |
| 2-benzofuryl | 70 | 105–107 |

PREPARATION Y

5-[(N-Hydroxy-N-carbamoyl) aminomethyl]-2[(5-methyl-2-(4-methylphenyl) oxazolyl)methyl] benzofuran A suspension of the product of Preparation X (4.83 g, 10.0 mmol) in ethanol (165 mL) was heated until homogeneous and ammonium formate (5.23 g, 82.9 mmol) and 10% Pd/C (1.19 g) was added. After 2 hours at room temperature, the reaction was heated to 50° C. and filtered through a pad of celite, the celite was then washed with several portions of hot ethanol and the combined organic layers concentrated to a yellow solid. This solid was then suspended in 250 mL water and the title compound (2.87 g, 73%) was then recovered by vacuum filtration as a yellow solid: mp 183°–185° C.

Also prepared by this method were 5-[(N-hydroxy-N-carbamoyl)aminomethyl]-2-](5-methyl-2-substituted-4-oxazolyl)methyl]benzofuran derivatives as follows:

| Substituent | Yield(%) | mp(°C.) |
|---|---|---|
| 2-furyl | 75 | 176–179 |
| phenyl | 41 | 178–180 | and 1-hydroxy-1-[4-(2-(5-methyl-2-substituted-4-oxazolyl) ethoxy)benzyl]urea derivatives as follows:

| Substituent | Yield(%) | mp(°C.) |
|---|---|---|
| 2-naphthyl | 100 | 165–170 |
| 2-benzofuryl | 48 | 177–178 |

We claim:
1. A compound of the formula

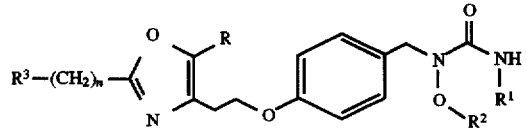

wherein

R is hydrogen or C$_1$ to C$_3$ alkyl;

R$^1$ is hydrogen or R$^4$ and R$^2$ is —COR$^5$ or —COOR$^5$;

R$^3$, R$^4$ and R$^5$ are each independently C$_1$ to C$_9$ alkyl, C$_3$ to C$_7$ cycloalkyl, phenyl, naphthyl, furyl, benzofuryl or thienyl or one of said groups mono- or disubstituted with C$_1$ to C$_3$ alkyl, C$_1$ to C$_3$ alkoxy, C$_1$ to C$_3$ alkoxycarbonyl, trifluoromethyl, fluoro or chloro; and n is 0 or 1; or a pharmaceutically acceptable cationic salt thereof.

2. A compound according to claim 1 wherein

R is methyl;

$R^2$ is —$COOR^5$; and n is 0.

3. A compound according to claim 2 wherein $R^3$ is methyl.

4. A compound according to claim 3 wherein $R^1$ is hydrogen; and $R^5$ is methyl, ethyl, 2-methylpropyl or phenyl.

5. A compound according to claim 3 wherein $R^1$ is $R^4$;

$R^4$ is phenyl, 1-methylethyl or ethoxycarbonylmethyl; and $R^5$ is methyl.

6. A compound of the formula

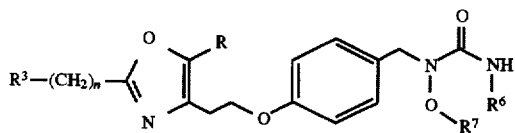

wherein

R is hydrogen or C1 to C3 alkyl;

$R^6$ is hydrogen or $R^3$;

$R^7$ is hydrogen or a conventional hydroxy protecting group;

each $R^3$ is independently C1 to C8 alkyl, C3 to C7 cycloalkyl, phenyl, naphthyl, furyl or thienyl, or one of said groups mono- or disubstituted with C1 to C3 alkyl, C1 to C3 alkoxy, C1 to C3 alkoxycarbonyl, trifluoromethyl, fluoro or chloro; and n is 0 or 1.

7. A compound according to claim 6 wherein

R is methyl;

$R^6$ is hydrogen; and n is 0.

8. A compound according to claim 7 wherein $R^3$ is phenyl, 2-methoxyphenyl, 4-trifluoromethylphenyl, 2-furyl or 2-benzofuryl; and $R^7$ is hydrogen.

9. A compound according to claim 7 wherein $R^3$ is phenyl, 2-methoxphenyl, 4-trifluoromethylphenyl, 2-furyl or 2-benzofuryl; and $R^7$ is benzyl.

10. A pharmaceutical composition for use in a hyperglycemic or hypercholesterolemic mammal, comprising, respectively, a blood glucose lowering or blood cholesterol lowering amount of a compound according to claim 1 and a pharmaceutically acceptable carrier.

11. A method of lowering the blood glucose in a hyperglycemic mammal comprising administering to said mammal a blood glucose lowering amount of a compound according to claim 1.

12. A method of lowering the blood cholesterol in a hypercholesterolemic mammal comprising administering to said mammal a blood cholesterol lowering amount of a compound according to claim 1.

13. A process for preparing a compound of the formula

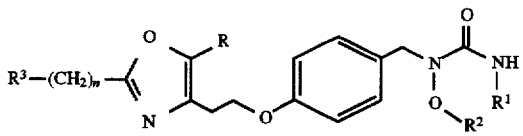

wherein

R is hydrogen or C1 to C3 alkyl;

$R^1$ is hydrogen or $R^4$ and $R^2$ is —$COR^5$ or —$COOR^5$;

$R^3$, $R^4$ and $R^5$ are each independently C1 to C9 alkyl, C3 to C7 cycloalkyl, phenyl, naphthyl, furyl, benzofuryl or thienyl or one of said groups mono- or disubstituted with C1 to C3 alkyl, C1 to C3 alkoxy, C1 to C3 alkoxycarbonyl, trifluoromethyl, fluoro or chloro; and n is 0 or 1;

comprising reacting a compound of the formula

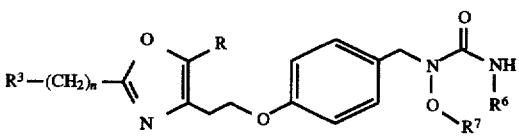

wherein R, $R^1$, $R^2$, R3, $R^4$, $R^5$ and n are as defined above and $R^6$ and $R^7$ are each hydrogen, with about one molar equivalent of a corresponding chloroformate or acid chloride having the formula $R^5OCOCl$, or $R^5COCl$, respectively, in the presence of a strong base in a reaction-inert solvent.

14. A process according to claim 13, wherein said base is NaOH or KOH and said solvent is aqueous.

15. A process according to claim 13, wherein said base is a tertiary amine and said solvent is organic.

* * * * *